United States Patent [19]

Kawamura et al.

[11] Patent Number: 4,820,268
[45] Date of Patent: Apr. 11, 1989

[54] TRANSFUSION APPARATUS

[75] Inventors: Takao Kawamura; Tetsuya Miyatake, both of Tokyo, Japan

[73] Assignee: Nikkiso Co., Ltd., Tokyo, Japan

[21] Appl. No.: 114,739

[22] Filed: Oct. 30, 1987

[30] Foreign Application Priority Data

Nov. 5, 1986 [JP] Japan ................. 61-262041

[51] Int. Cl.$^4$ ............................................. A61M 31/00
[52] U.S. Cl. ......................................... 604/67; 604/65
[58] Field of Search ................. 604/65, 67, 66, 251, 604/253, 153, 123, 122

[56] References Cited

U.S. PATENT DOCUMENTS

| 3,450,153 | 6/1969 | Hildebrandt et al. | 604/67 |
| 3,990,444 | 11/1976 | Vial | 604/123 |
| 4,018,362 | 4/1977 | Ubaud | 604/65 |
| 4,155,362 | 5/1979 | Jess | 604/123 |
| 4,261,388 | 4/1981 | Shelton | 604/65 |
| 4,355,638 | 10/1982 | Iwatschenko et al. | 604/65 |
| 4,397,642 | 8/1983 | Lamadrid | 604/65 |
| 4,645,489 | 2/1987 | Krumme et al. | 604/65 |
| 4,731,057 | 3/1988 | Tanaka et al. | 604/67 |

FOREIGN PATENT DOCUMENTS 50-108791 8/1975 Japan .
58-36562 3/1983 Japan .

Primary Examiner—C. Fred Rosenbaum
Assistant Examiner—Kathleen A. Daley
Attorney, Agent, or Firm—Robert R. Jackson

[57] ABSTRACT

A transfusion apparatus including a pump section for sequentially pressing and blocking a transfusion tube to feed a liquid, a detecting section for detecting a given cycle of pump operation in the pump section, and a drive-control for driving and controlling the pump section is disclosed, in which the transfusion tube on an upstream side above the pump section is provided with a dropping cylinder on which is arranged a detector for counting the number of droplets and that the apparatus is further provided with a comparator for comparing the number of droplets in the given cycle of the pump operation with a predetermined value to judge a type of a transfusion set.

4 Claims, 2 Drawing Sheets

F I G. 1
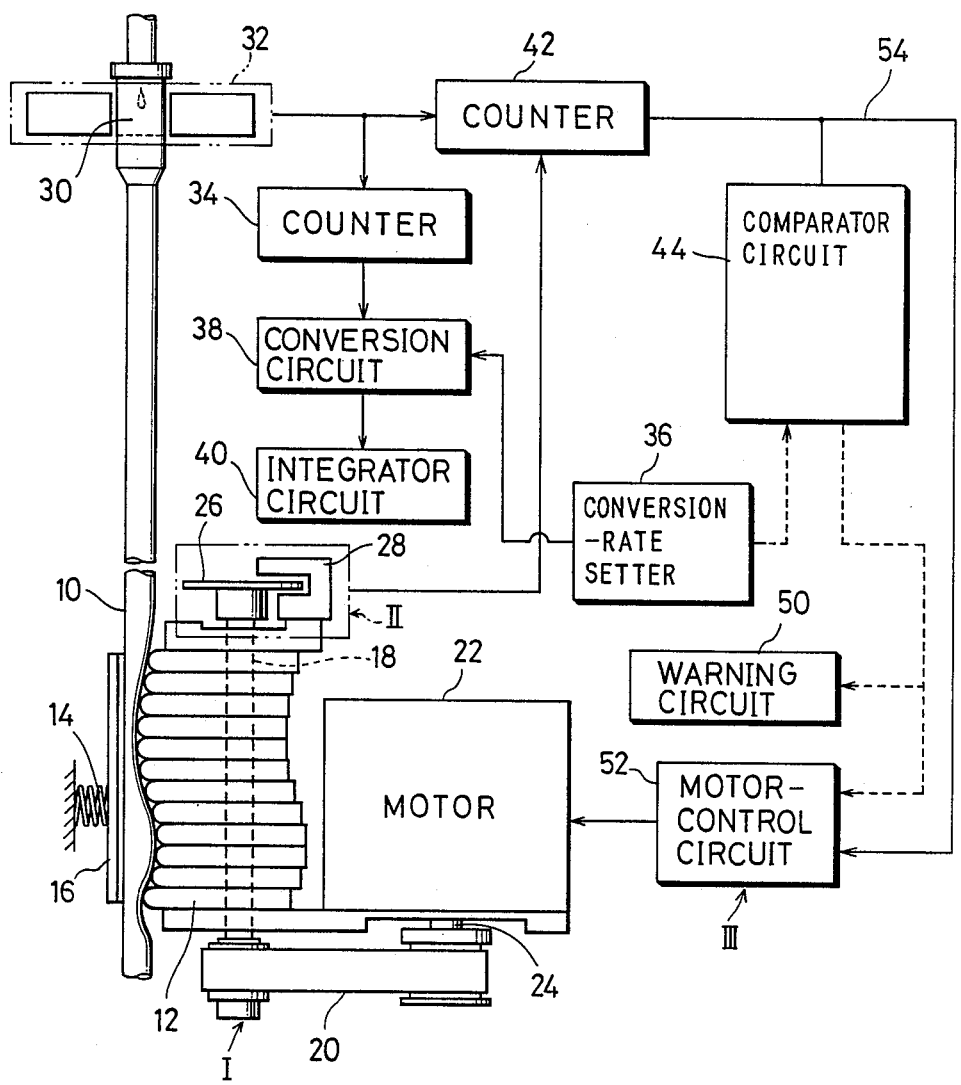

TRANSFUSION APPARATUS

FIELD OF THE INVENTION

This invention relates to a transfusion apparatus useful for an automatic dripping apparatus.

BACKGROUND OF THE INVENTION

There has been previously known a transfusion apparatus useful for an automatic dripping apparatus, in which a transfusion bottle is provided with a transfusion tube which at its portion has a dropping cylinder and on its downstream side is provided with a pump section having a peristaltic action on the tube.

In the transfusion apparatus of such type, monitoring of a quantity of the transfusion is very important for controlling the transfusion of a liquid to a patient. On such a view point, there has been utilized a mechanism in which the number of droplets in the dropping cylinder is counted while a conversion rate of the transfusion volume (the number of droplets per ml) inherent to a transfusion unit is determined for calculating the number of droplets as the transfusion volume.

In general, the conversion rate in a commercially available transfusion unit has been determined to be sixty droplets per ml in the transfusion set for children while fifteen droplets per ml for the adults. The number of droplets per ml in the practical transfusion set, however, is not always kept constant. As a result, in most hospitals utilizing the transfusion set, the conversion rate must be confirmed each time the transfusing operation is performed for resetting the conversion rate if necessary, resulting in the poor operability. Unless the conversion rate is not confirmed thereby resulting in uncorrect transfusion (for example, in case of employing the transfusion set for the adults based on the conversion rate (sixty droplets per ml) for children), about 4 times higher amount of the transfusion than the intended amount is introduced into the children.

Accordingly, an object of the invention is to provide a transfusion apparatus in which a transfusion tube at its predetermined range is subjected to a peristaltic movement in a pump section for feeding a volume of a liquid, based on which volume the number of droplets in a dropping cylinder is counted for discriminating the transfusion set for the adults or children, and further in which the conversion rate for the number of droplets corresponding to the transfusion amount may be conveniently judged, if necessary.

SUMMARY OF THE INVENTION

In order to achieve the above object, the invention provides a transfusion apparatus comprising a pump section for sequentially pressing and blocking a transfusion tube to feed a liquid, a detecting section for detecting a given cycle of pump operation in said pump section, and a drive-control section for driving and controlling said pump section, characterized in that the transfusion tube on an upstream side above the pump section is provided with a dropping cylinder on which is arranged a detector for counting the number of droplets and that the apparatus further comprises a comparator for comparing the of droplets in the given cycle of the pump operation w a predetermined value to judge a type of a transfusion set.

In the transfusion apparatus according to the invention, the detector for counting the number of droplets may comprise a drop sensor arranged at the dropping cylinder and a counter for counting output signals from the drop sensor as the number of droplets during the given cycle detected by a position detector in the pump section. In this case, the comparator preferably compares the number of droplets resulting from the output of the drop detector and the detecting section during the given cycle of the pump operation with the predetermined value to determine the numerical relation therebetween for discriminating the transfusion set for adults or for children.

Alternatively, the transfusion apparatus may comprise a first comparator for comparing the number of droplets in the given cycle of the pump operation with a predetermined value to judge a type of a transfusion set, and a second comparator for judging whether the number of droplets, which determines a conversion rate for a transfusion volume previously established depending on a judging output signal from the first comparator, is proper or not. In this case, the first comparator may compare the number of droplets resulting from the output of the drop detector and the detecting section during the given cycle of the pump operation with the predetermined value to determine the numerical relation for discriminating the transfusion set for adults or for children, while the second comparator may compare the number of droplets, which determines a conversion rate for a transfusion volume previously established depending on a judging output signal from the first comparator, with a referential value to determine the numerical relation therebetween for judging whether the transfusion set is applicable to the adults or children. Preferably, the second comparator generates a judging output signal for instructing operation of a warning circuit and stoppage of a controlling circuit of a pump-driving motor.

In accordance with the invention, the number of droplets during the given cycle of the pump section may be counted and compared with the predetermined value for reliably judging a type of the transfusion set. Further, after judging the type of the transfusion set, the conversion rate for the number of droplets corresponding to the transfusion volume may be conveniently evaluated for ensuring the safe control of the pump operation.

The transfusion apparatus according to the invention will now be described in more detail with reference to the accompanying drawings.

BRIEF DESCRIPTION OF THE DRAWINGS

FIG. 1 is a systematic view showing one embodiment of the transfusion apparatus according to the invention;

PREFERRED EMBODIMENTS OF THE INVENTION

Figure 2:
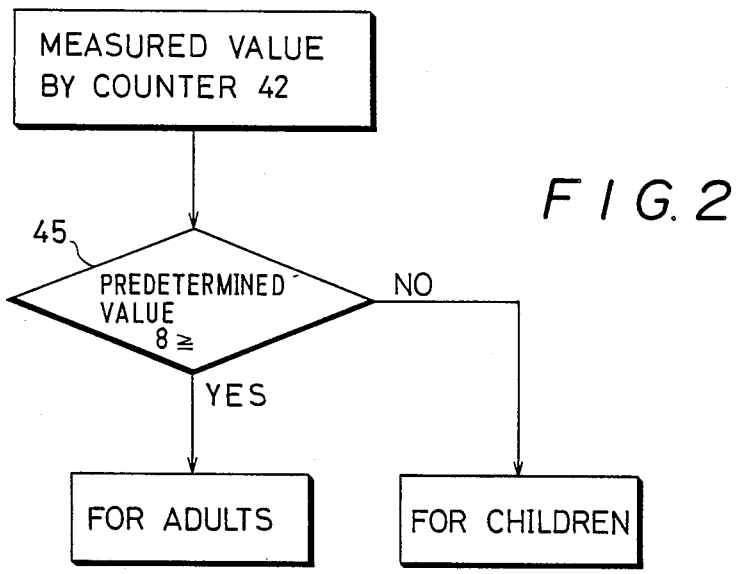
FIG. 2 is a flow chart showing one embodiment of a comparator circuit in FIG. 1.

Referring to FIG. 1, the transfusion apparatus according to the invention basically comprises a pump section I, a detecting section II, and a drive-control section III.

The pump section I contains an elastic transfusion tube 10, a plurality of peristaltic fingers 12 arranged on one side of the transfusion tube 10 for sequentially closing and opening its passage, a spring 14 arranged oppositely to the fingers 12 for securing the other side of the transfusion tube 10, and a presser plate 16 urged by the spring 14. Each finger 12 is supported by a holder (not shown) and is provided with a slit for positioning an eccentric cam through which a rotary shaft 18 passes for generating a required peristaltic movement. The adjacent cam on the upstream side secured to the rotary shaft 18 is imparted with a delayed angle of 360°, thereby converting the rotary movement of the eccentric cam to the linear movement of the fingers 12 for urging and feeding a liquid through the transfusion tube 10. For this purpose, the rotary shaft 18 at its one end is connected through a transmission mechanism 20 to a driving shaft 24 of a motor 20, while the other end is provided with a rotation-detecting disc 26 which in turn is provided with a rotational position detector 28 constituting the detecting section II.

The transfusion tube 10 of the pump section I thus constructed is provided on its upstream side with a dropping cylinder 30 and on a further upstream side with a transfusion bottle (not shown). The dropping cylinder 30 at its circumference is surrounded by a drop sensor 32 for detecting the dripping condition of the transfusion liquid and for generating output signals to be counted by a counter 34, thereby calculating the number of droplets which is then fed to a conversion circuit 38 and compared with a conversion rate determined by a conversion-rate setter 36 to calculate a volume of the transfusion liquid. Then, the calculated liqiud volume is integrated in an integrator circuit 40.

The construction as described hereinabove corresponds to a basic principle in a conventional transfusion pump of a drop-control type for calculating the number of droplets in a cylinder and converting the number to a volume of the transfusion liquid.

In accordance with the invention, one cycle of the peristaltic movement in the pump section I is detected by the position detector 28, while the output signals from the drop sensor 32 is counted by the counter 42, thereby determining the number of droplets during the one cycle of the pump operation. The value thus determined by the counter 42 is then fed to a comparator circuit 44 for judging a type of the transfusion set. In this embodiment, the comparator circuit 42 may be predetermined to a value (for example, "8") corresponding to the number of droplets, as shown in FIG. 2, in order to discriminate the transfusion set for the adults or children, which value is then compared with the measured counts in the comparator 45 to judge whether the predetermined value is higher or lower. A higher predetermined value than the measured counts indicates the transfusion set for the adults, while a lower predetermined value indicates the set for the children. Preferably, the judging output may be indicated by any suitable indicator means.

Figure 3:
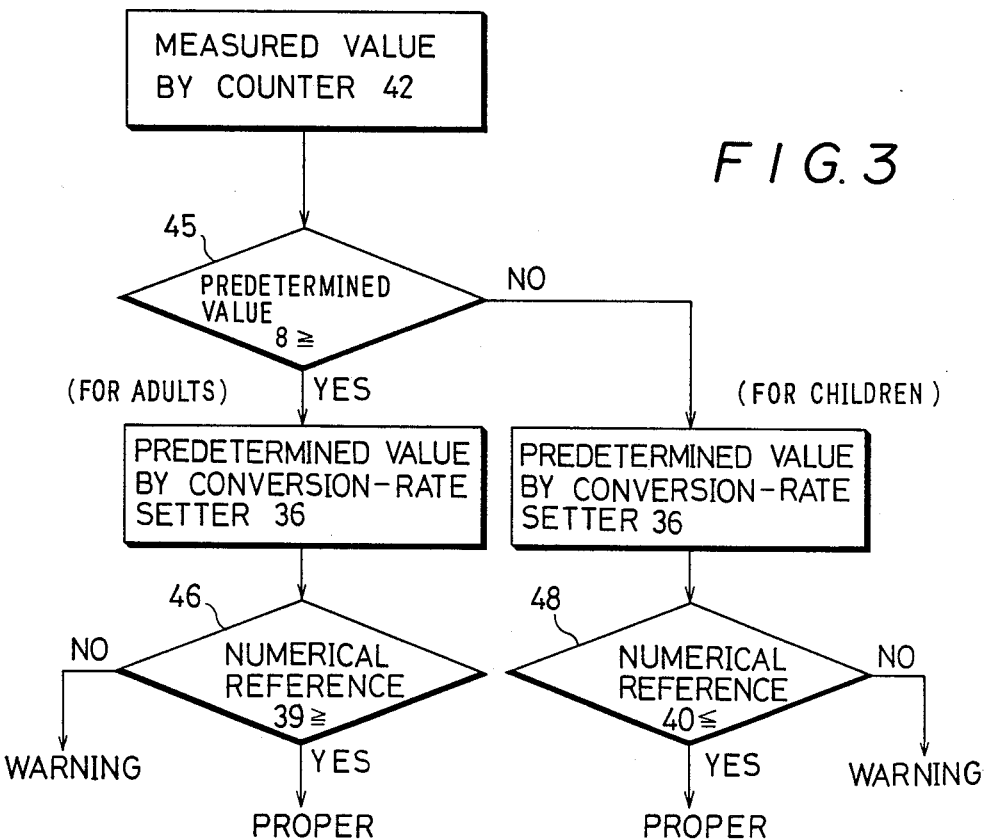
FIG. 3 is another flow chart showing an alternative embodiment of the comparator circuit.

In accordance with another embodiment of the invention, the predetermined value of the conversion rate relative to the transfusion volume established in the conversion-rate setter 36 may be judged for its properness. In this case, as shown in FIG. 3, the comparator circuit 44 allows the first comparator 45 to judge a type of the transfusion set similarly to the embodiment of FIG. 2 and thereafter allows the second comparator 46 or 48 to judge whether the predetermined value in the setter 36 is proper or not. For this purpose, the second comparator 46, 48 is inputted with the predetermined value of the comparison-rate setter 36, which is compared with a numerical reference (for example, "40" or "39"). In other words, for the transfusion set of the adults the predetermined value is compared with the reference "39" in the second comparator 46 for determining the properness of the transfusion set when the former is lower than the latter, while for the transfusion set for the children the predetermined value is compared with the numerical reference "40" in the second comparator 48 for determining the properness of the transfusion set when the former is higher than the latter. When the compared result is contrary to such evaluation in the judgment in the second comparator 46 or 48, the output signal therefrom may be fed to a warning circuit 50 and to a motor-control circuit 52 for instructing generation of a warning signal and stoppage of the motor control. Reference 54 represents a feed-back system from the drive-control section III to the pump section I.

The operation of the first comparator 45 and the second comparator 46, 48 will now be illustrated for its one embodiment with the actual results. The pump section was assembled using twelve fingers 12 each of 5 mm thickness and a transfusion tube 10 of an inner diameter 2.8 mm and an outer diameter 3.8 mm. Upon operation of the transfusion pump thus assembled, the number of droplets during one cycle was "3" or "4" for the adult transfusion set (1 ml=15 droplets), while it was "13", "14" or "15" for the child transfusion set (1 ml=60 droplets). Thus, the suitability of the transfusion set either for the adults or the children was readily and reliably judged by predetermining the value of "8" in the comparator 45. Similarly for the judgment of the predetermined value in the conversion-rate setter 36, the properness of the transfusion set either for the adults (1 ml=15 droplets) or the children (1 ml=60 droplets) was readily and reliably judged by predetermining the numerical references of "39" and "40".

It will be appreciated from the above that in accordance with the invention the transfusion set may conveniently and reliably judged by counting the number of droplets in the dropping cylinder during one cycle of the pump operation and comparing the resulting counts with the predetermined value for the judgment. Further, the comparison of the judged result with the predetermined value in the conversion-rate setter permits the proper judgment of the value. In case of the conversion rate being inconsistent, the warning signal may generated to discontinue the operation of the pump section. Thus, in accordance with the invention the transfusion volume may be properly monitored and controlled, while the risk of the incorrect drop volume may be reliably prevented for conveniently achieving the high safety of the transfusion management when handling various types of transfusion units.

What is claimed is:

1. A transfusion apparatus comprising a pump section for sequentially pressing and blocking a transfusion tube to feed a liquid, a detecting section for detecting a given cycle of pump operation in said pump section, and a drive-control section for driving and controlling said pump section, characterized in that the transfusion tube on an upstream side above the pump section is provided with a dropping cylinder on which is arranged a detector for counting the number of droplets, said detector comprising a drop sensor arranged at the dropping cylinder and a counter for counting output signals from said drop sensor as the number of droplets during said given cycle detected by a position detector in the pump section, said apparatus further comprising a comparator for comparing the number of droplets resulting from the output of the drop detector and the detecting section during said given cycle of the pump operation with a predetermined value to determine the numerical relation therebetween for discriminating the transfusion set for adults or for children.

2. A transfusion apparatus comprising a pump section for sequentially pressing and blocking a transfusion tube to feed a liquid, a detecting section for detecting a given cycle of pump operation in said pump section, and a drive-control section for driving and controlling said pump section, characterized in that the transfusion tube on an upstream side above the pump section is provided with a dropping cylinder on which is arranged a detector for counting the number of droplets and that the apparatus further comprises a first comparator for comparing the number of droplets in said given cycle of the pump operation with a predetermined value to judge a type of a transfusion set, and a second comparator for judging whether the number of droplets, which determines a conversion rate for a transfusion volume previously established depending on a judging output signal from said first comparator, is proper or not.

3. The transfusion apparatus according to claim 2, wherein the first comparator compares the number of droplets resulting from the output of the drop detector and the detecting section during the given cycle of the pump operation with the predetermined value to determine the numerical relation therebetweeen for discriminating the transfusion set for adults or for children, while the second comparator compares the number of droplets, which determines a conversion rate for a transfusion volume previously established depending on a judging output signal from said first comparator, with a referential value to determine the numerical relation therebetween for judging whether the transfusion set is applicable to the adults or children.

4. The transfusion apparatus according to claim 2, wherein the second comparator generates a judging output signal for instructing operation of a warning circuit and stoppage of a controlling circuit of a pump-driving motor.

* * * * *